(12) United States Patent
Kangasniemi et al.

(10) Patent No.: US 6,997,709 B2
(45) Date of Patent: Feb. 14, 2006

(54) DENTAL HAND INSTRUMENT AND TIP OF THE INSTRUMENT

(75) Inventors: Pekka Kangasniemi, Turku (FI); Eino Lumme, Pargas (FI); Kari Lehtonen, Turku (FI)

(73) Assignee: LM-Instruments Oy, Parainen (FI)

( * ) Notice: Subject to any disclaimer, the term of this patent is extended or adjusted under 35 U.S.C. 154(b) by 104 days.

(21) Appl. No.: 10/203,356

(22) PCT Filed: Feb. 14, 2001

(86) PCT No.: PCT/FI01/00143

§ 371 (c)(1),
(2), (4) Date: Aug. 9, 2002

(87) PCT Pub. No.: WO01/60279

PCT Pub. Date: Aug. 23, 2001

(65) Prior Publication Data

US 2003/0022131 A1    Jan. 30, 2003

(30) Foreign Application Priority Data

Feb. 14, 2000    (FI) ................................. 20000302

(51) Int. Cl.
*A61C 3/00*    (2006.01)
(52) U.S. Cl. .................................................... 433/147
(58) Field of Classification Search ............... 433/141, 433/146, 147, 142, 143, 144, 164
See application file for complete search history.

(56) References Cited

U.S. PATENT DOCUMENTS

| 1,187,497 | A | * | 6/1916 | Canfield ...................... 279/48 |
| 1,626,519 | A | * | 4/1927 | Dunlop ....................... 279/102 |
| 3,325,900 | A | | 6/1967 | Sohlberg ....................... 32/46 |
| 3,411,211 | A | | 11/1968 | Fountain ....................... 32/46 |
| 3,935,640 | A | | 2/1976 | Cohan .......................... 32/40 |
| 4,030,199 | A | * | 6/1977 | Russell ....................... 433/147 |
| 4,552,531 | A | * | 11/1985 | Martin ....................... 433/147 |
| 4,586,901 | A | | 5/1986 | Tanaka et al. .............. 433/164 |

(Continued)

FOREIGN PATENT DOCUMENTS

WO    97/38644 A1    10/1997

*Primary Examiner*—Cary E. O'Connor
(74) *Attorney, Agent, or Firm*—Kubovcik & Kubovcik (57) ABSTRACT

A dental hand instrument (10), comprising a handle (11) with parts (12a, 12b) at its ends. The end of each neck part is provided with a coupling element (15) designed for the connection of replaceable tips (20) and oriented in the same direction with the neck part. The coupling element is a socket or pin (19) extending in the same direction with the neck part and allowing a corresponding concentric pin (21) or socket (26) of the tip to be fitted into/onto it. The socket of the coupling element may be provided with slots (17), and the inner surface of the socket has a circular or cornered cross-sectional form. The neck part and coupling element of the hand instrument are preferably made of stainless steel and the tip is made of steel, aluminum, plastic-coated aluminum, steel or titanium.

12 Claims, 10 Drawing Sheets

U.S. PATENT DOCUMENTS

| | | | |
|---|---|---|---|
| 4,992,048 A | 2/1991 | Goof | 433/102 |
| 5,028,234 A | 7/1991 | Schweitzer et al. | 433/147 |
| 5,178,537 A * | 1/1993 | Currie | 433/72 |
| 5,781,958 A * | 7/1998 | Meessmann et al. | 15/167.1 |
| 5,899,693 A | 5/1999 | Himeno et al. | 433/119 |
| 6,186,786 B1 * | 2/2001 | Trushkowsky | 433/164 |
| 6,371,764 B1 * | 4/2002 | Brave | 433/224 |
| 6,821,121 B1 * | 11/2004 | Rosen | 433/142 |

* cited by examiner

DENTAL HAND INSTRUMENT AND TIP OF THE INSTRUMENT

SUBJECT OF THE INVENTION

The invention relates to a hand instrument for use in dental care, comprising a handle having at each end of it a narrower neck part, preferably made of a high-strength metal such as steel, each neck part being provided with a tip forming a tool for dental care.

STATE OF THE ART

A dental hand instrument usually comprises a handle with a dental tool at least at one end of it. The handle may be made of metal, such as stainless steel, or a hard plastic material. However, the handle may also have a metal core coated with a softer material, such as silicone rubber. The handle and the tool are usually connected by neck parts bent in various ways to allow the tool to be applied even to difficult places, such as e.g. the hind surfaces of teeth. The neck part and the tool are generally joined to each other and made of the same material, e.g. stainless steel. The tool at the end of the hand instrument is e.g. a spicular feeler or a gingival pocket gauge, a scalpel for removal of dental calculus, a curette, a grooving tool, an evener, a filling dabber or a knife.

However, a dentist additionally needs other types of hand instrument besides those made of steel in his/her work. For instance, for pressing a dental filling in place, tools made of an elastic material and also of a transparent material are needed. Transparent tools are advantageous because plastic dental fillings can be hardened by applying ultraviolet light directly through a transparent pressing tool. Because of such requirements, dental hand instruments made entirely of plastic have been produced.

Often, however, it is not possible to have the entire hand instrument made of transparent and elastic material because the instrument would be too flexible. The instrument should be sufficiently rigid and sturdy to allow proper working. Therefore, instruments with a replaceable tip have been produced. An example of this type of solutions is the hand instrument presented in EP patent 0 079 299, in which a forceps-like coupling element at the end of a straight handle holds a transversely mounted curved tip made of transparent plastic and designed for the shaping of a dental filling. However, such a hand instrument is unpractical because the forceps-like structure is clumsy. With a tip mounted transversely on the end of the handle it is not possible to reach difficult places, such as e.g. the hind faces of teeth. With such an instrument it is also difficult to apply a sufficient force to the tooth to press a filling.

There are also gingival pocket gauges made completely of plastic, as well as plastic tips for a hand instrument having a long plastic neck part. Such a tip is connected to the handle with a screwed joint. However, the long plastic neck part has the disadvantage of being easily bent. For this reason, a hand instrument like this cannot be used in precision work.

OBJECT OF THE INVENTION

The object of the present invention is to achieve a new dental hand instrument having none of the drawbacks described above.

FEATURES CHARACTERISTIC OF THE HAND INSTRUMENT OF THE INVENTION

The dental hand instrument of the invention is characterized in that
  the end of each neck part of the hand instrument is provided with a coupling element, preferably a dead hole, pin or pointed part, oriented in the same direction with the neck part and concentric with it,
  that replaceable tips, which are replaceable dental tools, preferably made of a different material than the neck parts, preferably of plastic or metal, can be coupled to the coupling elements at the ends of the neck parts,
  and that the replaceable tips are provided with counterparts, preferably clutches or sockets matching the coupling elements of the neck parts, oriented in the same direction with the neck parts and concentric with them.

The invention combines the best qualities, such as thinness, ductility and stiffness, of a neck part made from a high-strength metal, such as steel, with the best qualities of another material of the tip, which are needed in relevant clinical work. Thus, the tip can be replaced as required with another one that is best suited for the work on hand in respect of tool shape and material.

The replaceable tips are connected to the ends of the neck parts of the hand instrument with concentric coupling elements oriented in the same direction with the neck parts, said replaceable dental tools forming a direct extension of the neck parts. Thus, the user of the hand instrument can apply working movements directly from the handle to the dental tool. The replaceable tips thus provide the same firmness and working precision as do tools fixedly attached to the ends of the neck parts of the hand instrument.

EMBODIMENTS OF THE HAND INSTRUMENT OF THE INVENTION

A preferred embodiment of the hand instrument of the invention is characterized in that
  each neck part of the hand instrument has an axial, socket-like coupling element at its end, forming an extension of it, inside which the axial projections matching the coupling elements of the tips can be fitted,
  and that the socket of the coupling element of each neck part has at least one groove or slot extending in the longitudinal direction of the socket.

A second embodiment of the hand instrument of the invention is characterized in that the axial socket of each neck part of the hand instrument has at least two slots extending in the longitudinal direction of the socket so that each coupling element has two opposite spring-like tongues which squeeze the projection of the tip between them.

A third preferred embodiment of the hand instrument of the invention is characterized in that the interior surfaces of the socket-like coupling elements of the neck parts have a circular or cornered cross-sectional form.

A fourth preferred embodiment of the hand instrument of the invention is characterized in that the interior surfaces of the socket-like coupling elements of the neck parts have a quadrangular or hexagonal cross-sectional form.

A fifth preferred embodiment of the hand instrument of the invention is characterized in that the coupling elements forming an extension of the neck parts comprise projections onto which the socket parts comprised in the tips can be fitted.

A sixth preferred embodiment of the hand instrument of the invention is characterized in that the projections of the coupling elements forming an extension of the neck parts are provided with at least one locking flange extending in the longitudinal direction of the projection.

A sixth preferred embodiment of the hand instrument of the invention is characterized in that the projections of the coupling elements forming an extension of the neck parts have a circular or cornered cross-sectional form.

Yet another preferred embodiment of the hand instrument of the invention is characterized in that the neck parts are made of a material, such as steel, that can be bent so as to change the position of the replaceable tips connected to them in relation to the handle of the hand instrument.

TIP OF THE HAND INSTRUMENT

The invention also concerns a tip of a dental hand instrument. The tip of a dental hand instrument of the invention is characterized in that
the tip of the dental hand instrument is a replaceable dental tool separate from the neck part and made of a different material, preferably plastic or metal, than the neck parts of the hand instrument, which are made of a high-strength metal, preferably steel,
and that the replaceable tip comprises a counterpart, preferably a projection or socket, matching the coupling elements at the ends of the neck parts of the hand instrument and extending in the same direction with the coupling element and being concentric with it.

EMBODIMENTS OF THE TIP OF THE HAND INSTRUMENT

A preferred embodiment of the tip of the hand instrument of the invention is characterized in that the replaceable tip comprises an axial projection which can be at least partially fitted into a socket-like coupling element forming an extension of the neck part of the hand instrument.

A second preferred embodiment of the tip of the hand instrument of the invention is characterized in that the axial projection of the replaceable tip is provided with at least one locking flange extending in the longitudinal direction of the projection, which flange can be fitted into a corresponding groove or slot in the socket-like coupling element forming an extension of the neck part of the hand instrument. Such a solution is advantageous when rotation of the tip is to be prevented.

A third preferred embodiment of the tip of the hand instrument of the invention is characterized in that the axial projection of the replaceable tip is provided with at least two locking flanges extending in the longitudinal direction of the projection which can be fitted into corresponding grooves or slots in the socket-like coupling element forming an extension of the neck part of the hand instrument. The locking flanges ensure that the tip cannot rotate. If correctly designed, the locking flange also effectively prevents the tip from getting out of the socket while the dentist is working.

A fourth preferred embodiment of the tip of the hand instrument of the invention is characterized in that the axial projection of the replaceable tip has a circular or cornered cross-sectional form.

A fifth preferred embodiment of the tip of the hand instrument of the invention is characterized in that the axial projection of the replaceable tip has a quadrangular or hexagonal cross-sectional form.

A sixth preferred embodiment of the tip of the hand instrument of the invention is characterized in that the replaceable tip comprises a socket which can be fitted onto the projection of the coupling element forming an extension of the neck part of the hand instrument.

A sixth preferred embodiment of the tip of the hand instrument of the invention is characterized in that the replaceable tip is made of e.g. plastic, aluminum, plastic-coated aluminum, steel or titanium.

Yet another preferred embodiment of the tip of the hand instrument of the invention is characterized in that the replaceable tip is made of a material, such as plastic or steel, that can be bent so as to allow the replaceable dental tool held in the tip to be turned into a desired position relative to the handle of the hand instrument.

EXAMPLES OF EMBODIMENTS

In the following, the invention will be described by the aid of examples with reference to the attached drawings, wherein

LIST OF ILLUSTRATIONS

DESCRIPTION OF ILLUSTRATIONS

Figure 1:
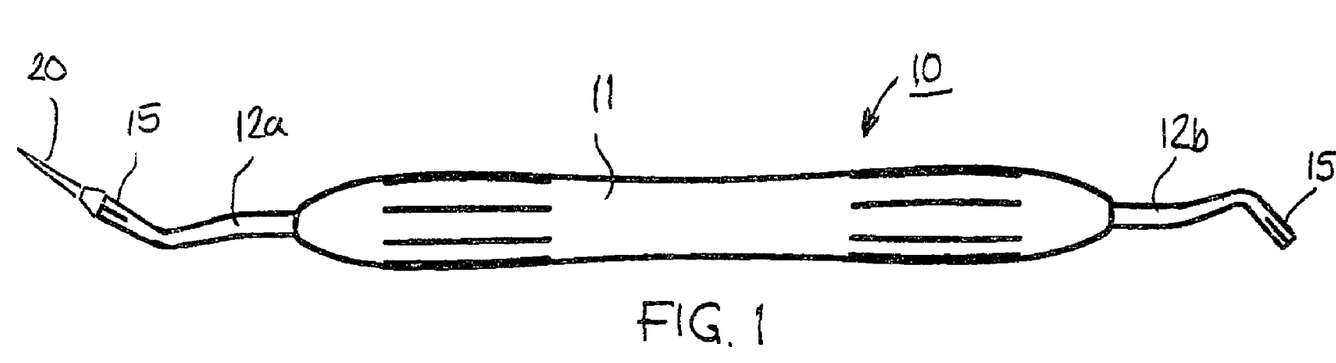
FIG. 1 presents a side view of an instrument according to the invention.

FIG. 1 presents a hand instrument 10 according to the invention. The instrument comprises neck parts 12a and 12b, one at each end of a handle 11, each neck part having a coupling element 15 at its end to accommodate replaceable tips. The handle 11 may be made of metal, e.g. stainless steel, or hard plastic. However, the handle 11 may also consist of e.g. a metallic core coated with a soft material, such as e.g. silicone rubber. The neck parts 12a and 12b are preferably made of stainless steel. In the example presented in FIG. 1, the neck parts 12a and 12b have been bent so that the tips 20 attached to them will be oriented in a direction only slightly differing from the direction of the handle 11.

Connected to the neck part 12a at the left-hand end in FIG. 1 is a tip 20, which is made of a different material than the neck parts 12a made of e.g. stainless steel. The material of the tip 20 is selected to suit the intended use, the material being e.g. plastic, aluminum, Teflon-coated aluminum, steel or titanium. A tip 20 made of a soft material is used e.g. when it is desirable to avoid damaging a titanium implant or a gingival pocket. A transparent material is used e.g. to harden plastic with UV light in connection with filling a tooth or building a dental column. In the example presented in FIG. 1, the tip 20 is a gingival pocket gauge made of plastic. However, the tip 20 may also be made of a hard material e.g. in the case of a tip used as a tool for working a tooth or filling.

Figure 2:
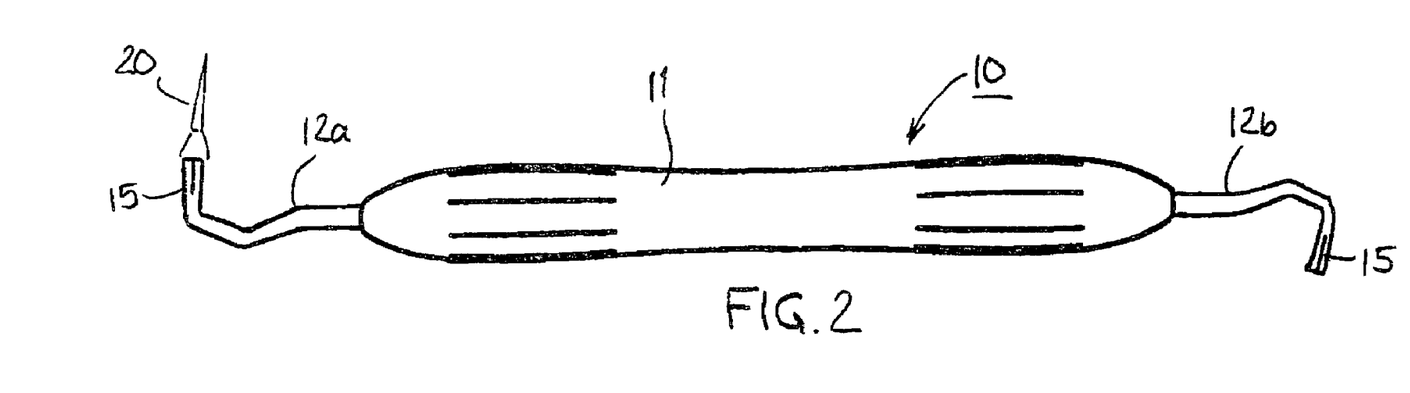
FIG. 2 corresponds to FIG. 1 and presents a second embodiment of the hand instrument.

FIG. 2 presents a hand instrument 20 differing from the instrument in FIG. 1 in that the neck parts 12a and 12b have been bent into a steeper curvature. In this case, the tips 20 connected to the coupling elements 15 are oriented in a direction almost perpendicular to the direction of the handle 11.

Figure 3:
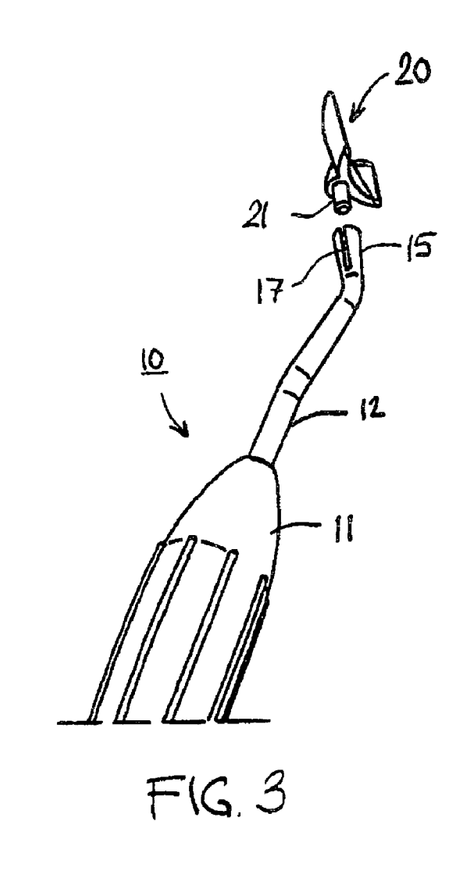
FIG. 3 presents an axonometric view of one end of the hand instrument and a tip to be attached to it.

FIG. 3 shows part of the handle 11 of the hand instrument 10 and a neck part 12 with a socket-like coupling element 15 at its end. A tip 20 made of e.g. plastic is connected to the coupling element 15 by inserting the projection 21 of the tip 20 into the socket-like coupling element 15 provided with a slot 17.

Figure 4:
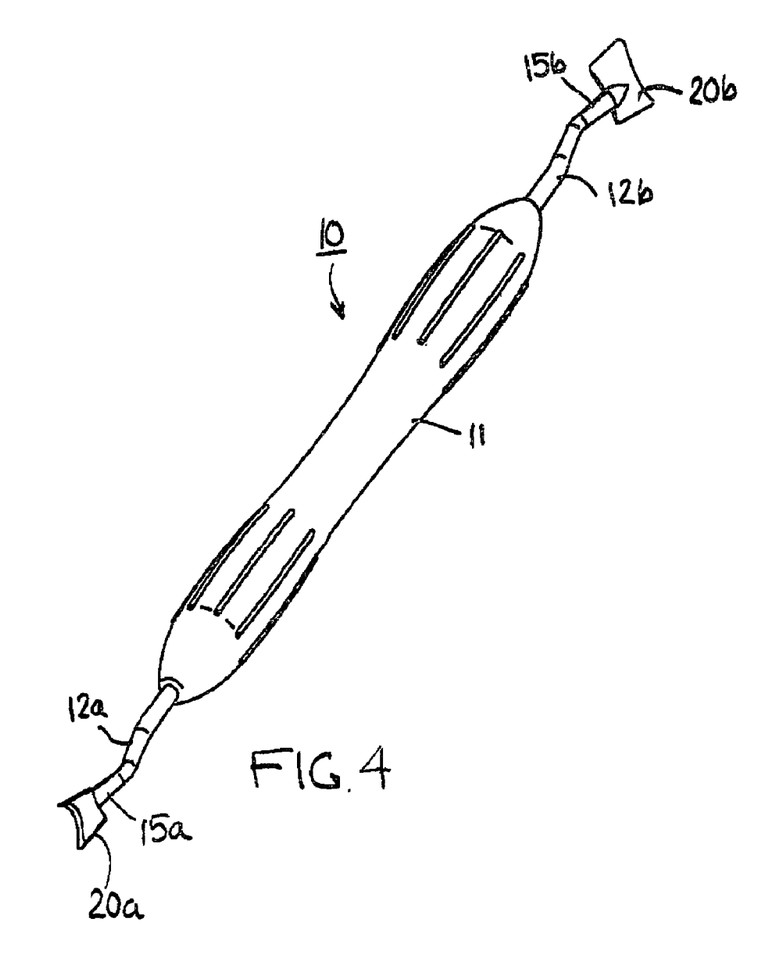
FIG. 4 presents an axonometric view of a hand instrument with a detachable tip attached to each end.

FIG. 4 presents an example in which the hand instrument 10 has plastic tips 20a and 20b connected to the coupling elements 15a and 15b of the steel neck parts 12a and 12b at both ends of the instrument.

Figure 5:
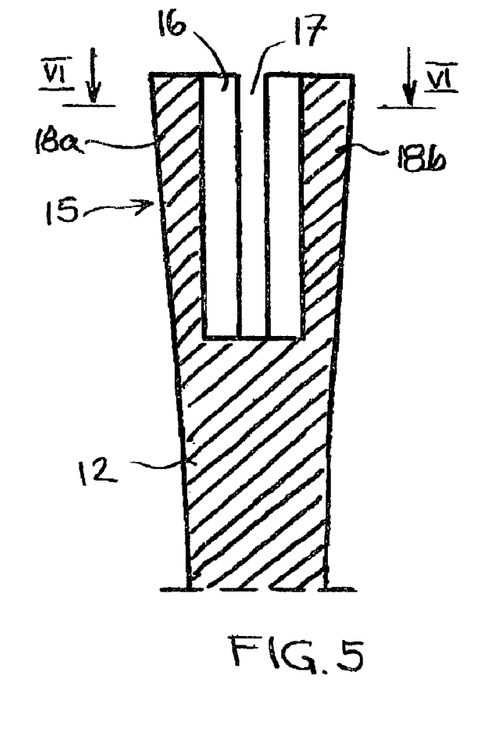
FIG. 5 presents a sectioned side view of a coupling element connected to the end of the neck part.

FIG. 5 presents a sectional view of an example of a coupling element 15 at the end of a steel neck part 12 of the hand instrument 10. The figure shows that this coupling element 15 has a socket-like structure. Inside the coupling element 15 there is an elongated space 16 having a round cylindrical form and divided longitudinally into two parts with slots 17. This space 16 may also have a slightly conical shape. An essential feature of the coupling element 15 presented in FIG. 5 is that the two halves 18a and 18b act like springs, squeezing the mounting projection of the tip inserted between them so as to hold it firmly in position.

Figure 6:
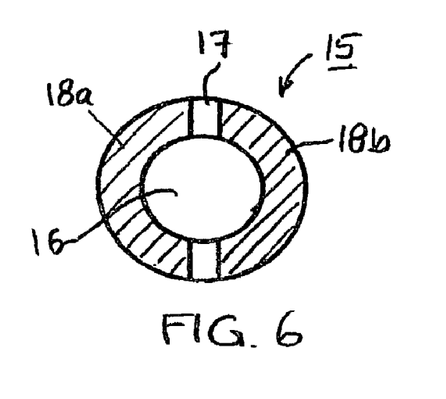
FIG. 6 presents a section of FIG. 4, taken along line VI—VI.

FIG. 6 presents a cross-section of the coupling element 15 shown in FIG. 5. It can be seen from the figure that the socket-like coupling element 15 has a mainly cylindrical space 16 inside it. The socket of the coupling element 15 is divided longitudinally into two parts 18a and 18b with slots 17. When the projection 21 of the tip 20 is inserted into the cylindrical space 16, the socket halves 18a and 18b squeeze it between them, holding it firmly in place. As the coupling element 15 has a symmetrical structure, the tip 20 can be inserted in two different positions into the cylindrical space 16 inside the coupling element 15.

Figure 7:
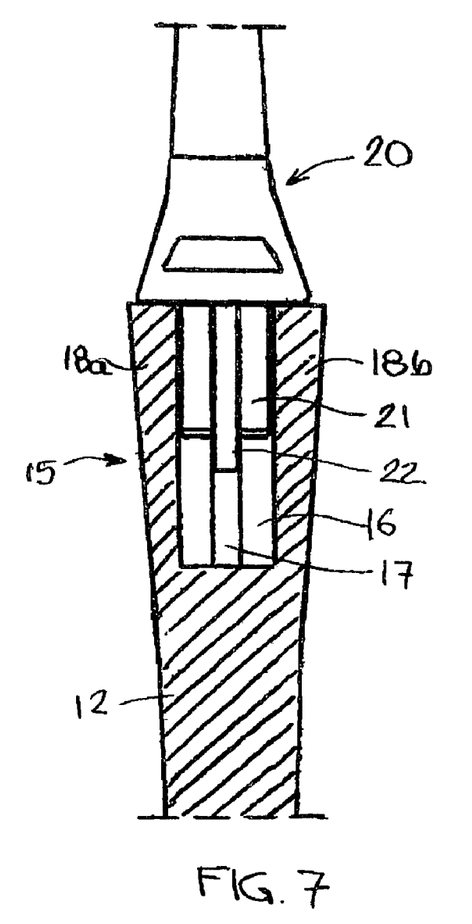
FIG. 7 corresponds to FIG. 5 and presents a tip provided with a locking flange, connected to the coupling element of the neck part.

FIG. 7 shows the end of a neck part 12 of the hand instrument 10 together with a coupling element 15 comprised in it, with a tip 20 inserted into the coupling element. The tip 20 is provided with a projection 21 matching the cylindrical space 16 and, in this example, provided with locking flanges 22 adapted to the slots 17. The locking flanges 22 prevent the tip 20 from rotating in relation to the neck part 12 of the hand instrument 10. A solution of this type is advantageous in cases where rotation of the tip 20 is not to be allowed. On the other hand, if it is desirable that the tip 20 be free to rotate while the dentist is working, then a tip 20 with a projection 21 having no locking flanges 22 is used.

Figure 8:
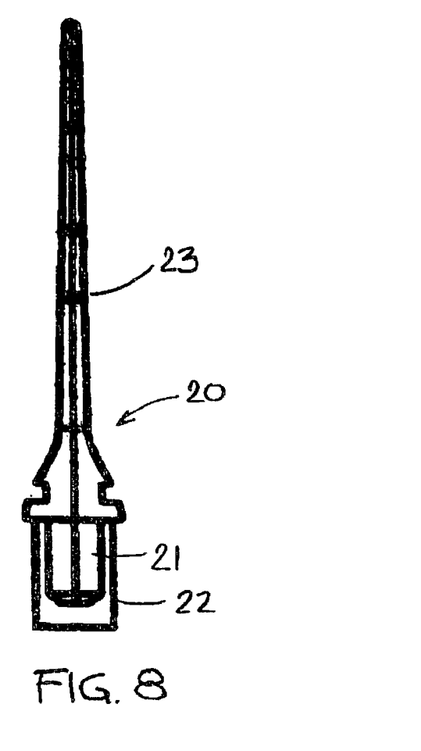
FIG. 8 presents a side view of a tip of the hand instrument, provided with a locking flange.

FIG. 8 presents a tip 20 for the hand instrument 10 which is a gingival pocket gauge provided with indicator rings 23. The projection 21 of the tip 20 and its locking flanges 22 holding the tip 20 unrotatable in the neck part 12 comprised in the handle 11 of the hand instrument 10 are clearly visible in the figure. The material of this tip 20 may be e.g. plastic, metal or plastic coated metal.

Figure 9:
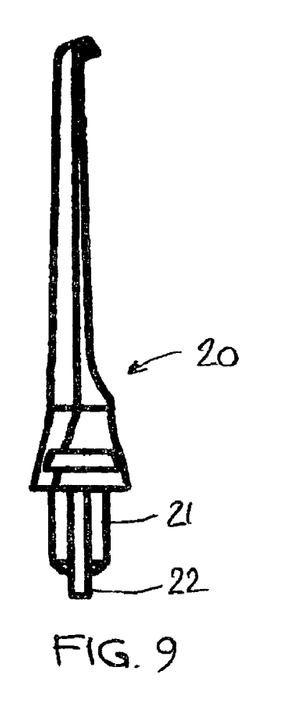
FIG. 9 corresponds to FIG. 8 and presents a second embodiment of the tip.
Figure 10:
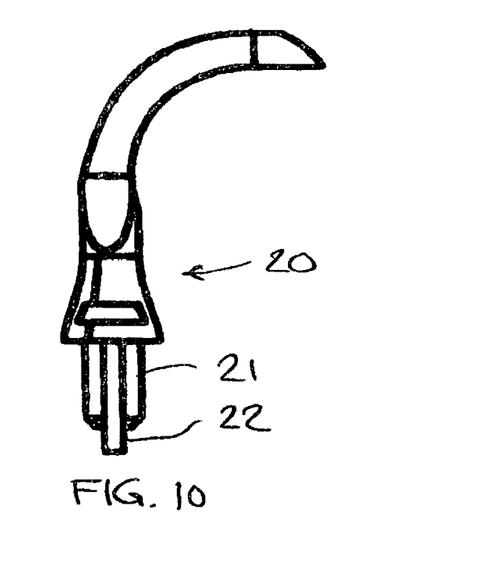
FIG. 10 corresponds to FIG. 8 and presents a third embodiment of the tip.
Figures 11, 12, 16:
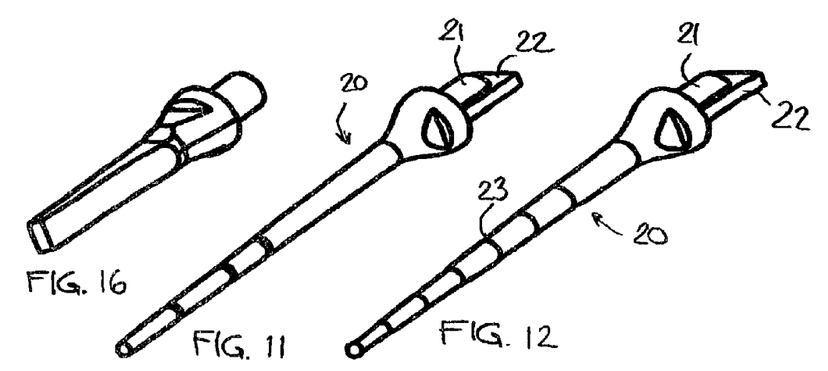
FIG. 11 presents an axonometric view of the tip shown in FIG. 8.
FIG. 12 corresponds to FIG. 11 and presents an axonometric view of a fourth embodiment of the tip.
FIG. 16 presents an axonometric view of a sixth embodiment of the tip without locking flanges.
Figures 13, 14, 15:
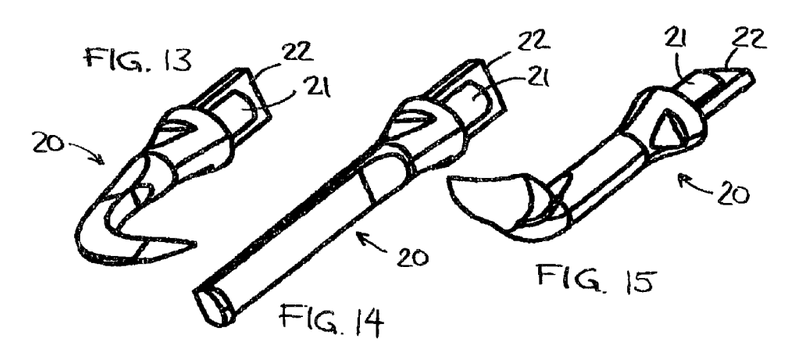
FIG. 13 presents an axonometric view of the tip shown in FIG. 10.
FIG. 14 presents an axonometric view of the tip shown in FIG. 9.
FIG. 15 corresponds to FIG. 14 and presents a fifth embodiment of the tip.
Figure 17:
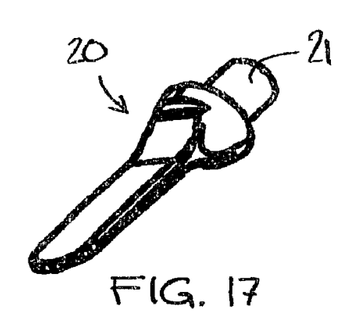
FIG. 17 corresponds to FIG. 16 and presents an axonometric view of a seventh embodiment of the tip.
Figure 18:
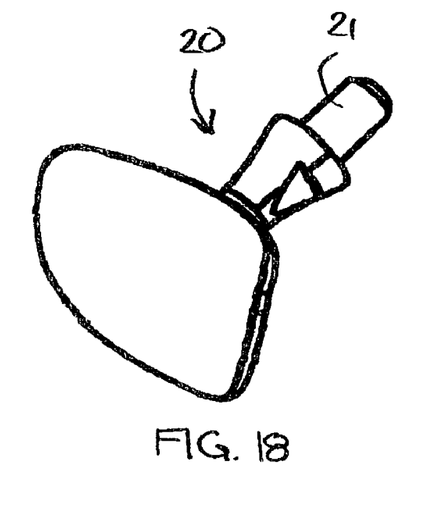
FIGS. 18–21 correspond to FIG. 16 and present embodiments of the tip in axonometric view.
Figure 19:
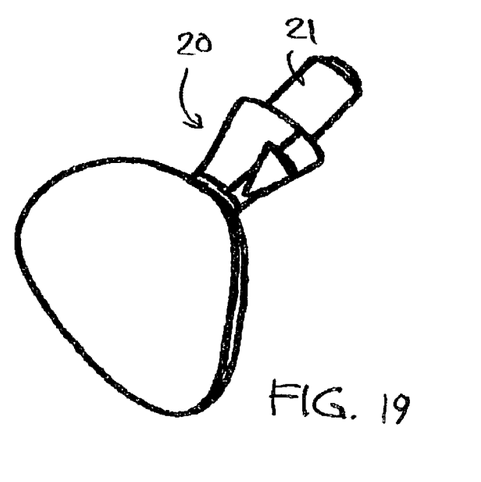

FIGS. 9–15 show different tips 20 with locking flanges 22 preventing rotation. FIGS. 9 and 14 present a hooked tip, FIGS. 10 and 13 a scalpel and FIGS. 11 and 12 show different types of gingival pocket gauge. The material used in these tips may be varied depending on the intended use.

Figure 20:
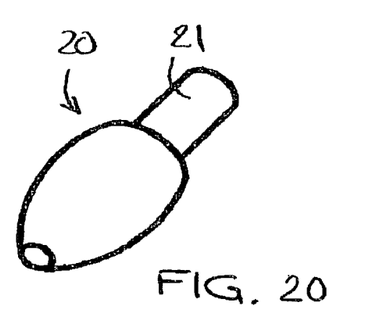
Figure 21:
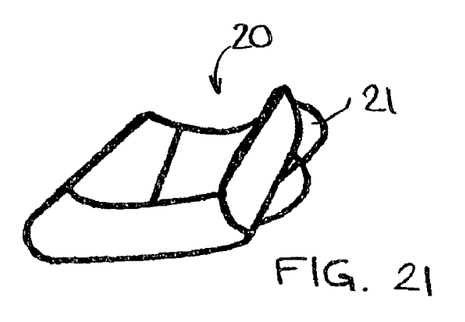
Figure 22:
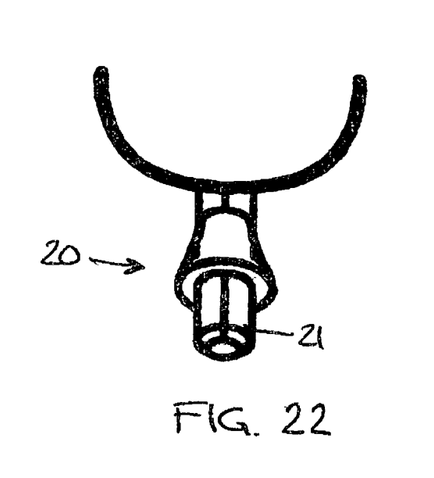
FIGS. 22 and 23 present side views of embodiments of the tip without locking flanges.
Figure 23:
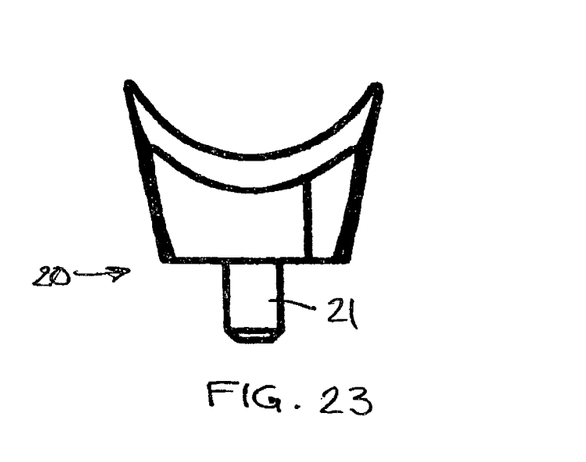
Figure 24:
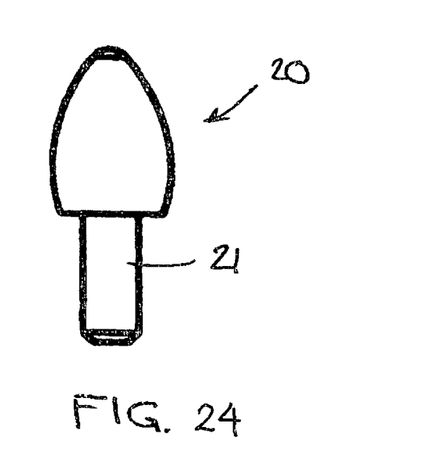
FIG. 24 presents a side view of the tip shown in FIG. 20.

FIGS. 16–24 again show examples of tips 20 which have no locking flanges and are therefore free to rotate when inserted into the coupling element 15. The tips in FIGS. 18, 19, 21 and 22 are matrix pressing tools used in filling a tooth. FIG. 23 shows a gingival retractor and FIGS. 20 and 24 show forming tools.

Figures 25, 26:
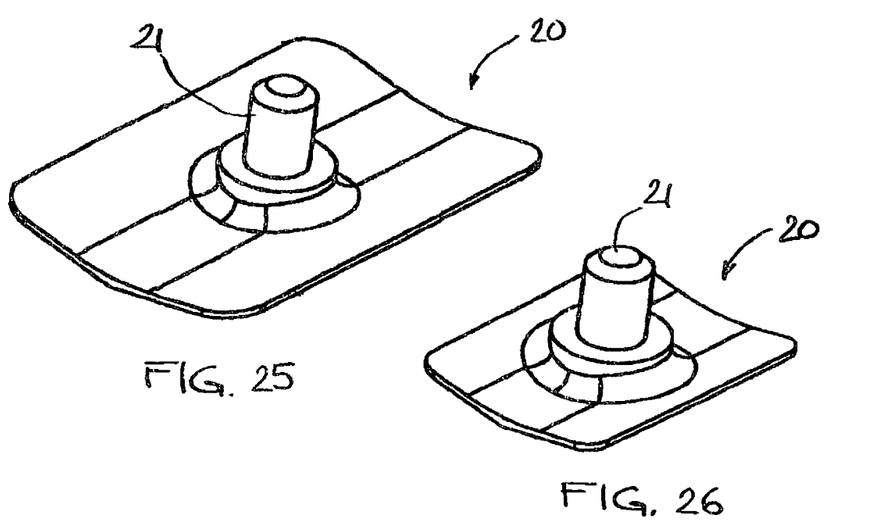
FIGS. 25 and 26 present axonometric views of tips used in filling a tooth.

FIGS. 25 and 26 present two tips 20 of different sizes used for pressing a dental filling. These tips have a round mounting projection 21, so they can rotate freely.

Figure 27:
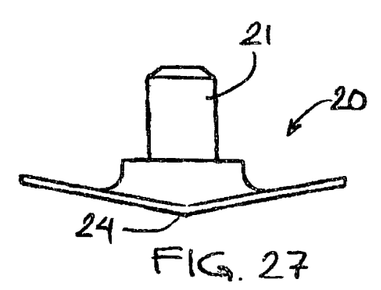
FIGS. 27 and 28 present side views of the tips shown in FIGS. 25 and 26.
Figure 28:
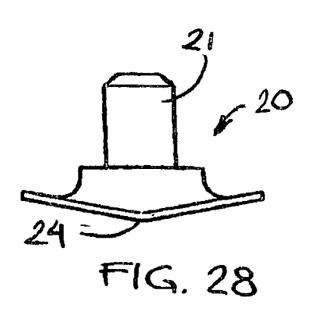

FIGS. 27 and 28 show the tips 20 of FIGS. 25 and 26 in side view. Both tips 20 have planar surfaces with an angle 24. When a filling in a molar tooth is pressed with the tip 20, the angle 24 orients itself in the direction of the indentation of the molar tooth.

Figure 29:
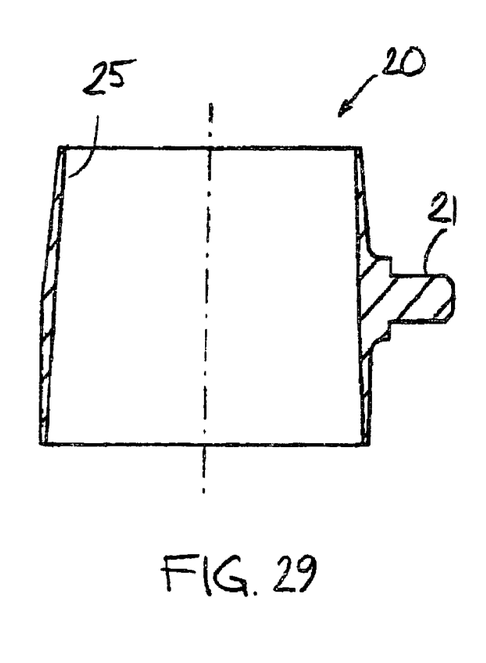
FIGS. 29–31 present sectional side views of tips implemented as column building rings.
Figure 30:
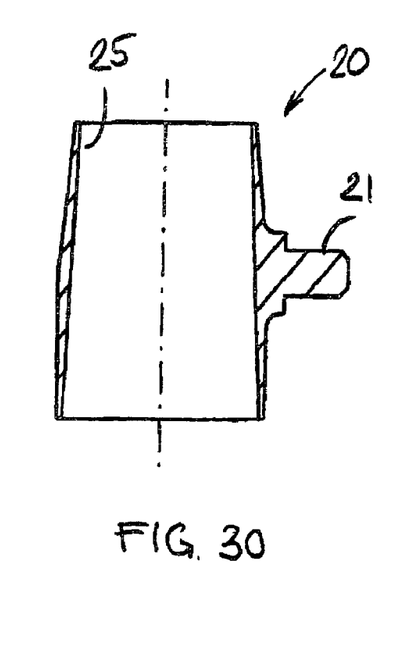
Figure 31:
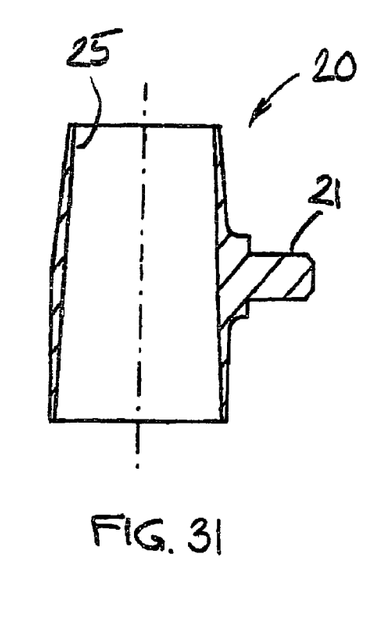

FIGS. 29–31 present three tips 20 implemented as column building rings of different sizes. They are provided with round mounting projections 21, so the tips 20 can rotate freely. The rings 25 designed for column building have a conical inner surface.

Figure 32:
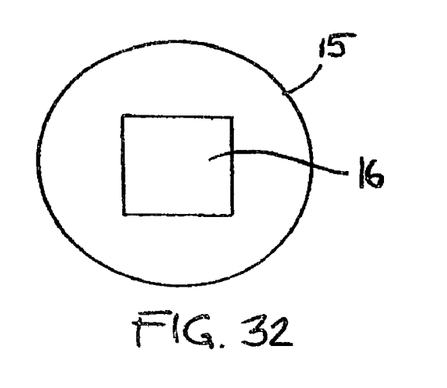
FIG. 32 presents a cross-section of the coupling element at the end of the neck part of the hand instrument according to the second embodiment.

FIG. 32 presents a second embodiment of the coupling element 15 at the end of the neck part 12 of the hand instrument 10, in which the cylindrical space 16 has a square cross-sectional form. In this case, the mounting projection 21 of the tip 20 connected to the coupling element 15 correspondingly also has a square cross-sectional form. The square form prevents rotation of the tip 20, so the cornered form provides the same effect as the slots 17 presented in FIG. 6. However, a square form has the advantage of allowing the tip 20 to be inserted in four different positions into the coupling element 15.

Figure 33:
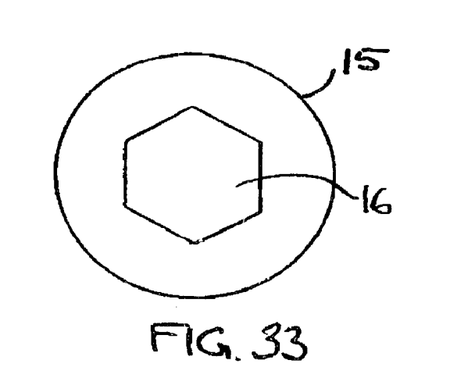
FIG. 33 corresponds to FIG. 32 and presents a cross-section of the coupling element according to the third embodiment.

In the example presented in FIG. 33, the cylindrical space 16 has a hexagonal cross-sectional form, which also prevents the rotation of the tip 20. The hexagon permits the tip 20 to be inserted in six different positions into the coupling element 15.

In the examples presented above, the coupling element 15 at the end of the neck part 12 of the handle 11 of the hand instrument 10 has a cylindrical space 16 of a round or cornered, e.g. quadrangular or hexagonal cross-section. However, the mutually matching parts of the coupling element 15 and tip 20 can also be implemented conversely so that the coupling element 15 is provided with a pin and the tip 20 is provided with a socket.

Figure 34:
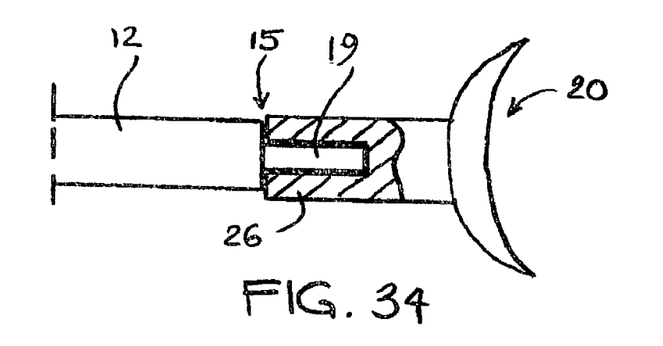
FIG. 34 presents a partially sectioned side view of the coupling element at the end of the neck part together with a tip attached to it, according to the fourth embodiment.

FIG. 34 presents a coupling element 15 of a hand instrument 10 having a pin 19 instead of a socket-like part at the end of the neck part 12. In this case, the tip 20 is correspondingly provided with a socket 26 matching the pin 19. The pin 19 and the socket 26 may have a round or cornered, e.g. quadrangular or hexagonal cross-sectional form. Cornered cross-sectional forms provide the same choices of varying the position of the tip 20 as explained above.

Figure 35:
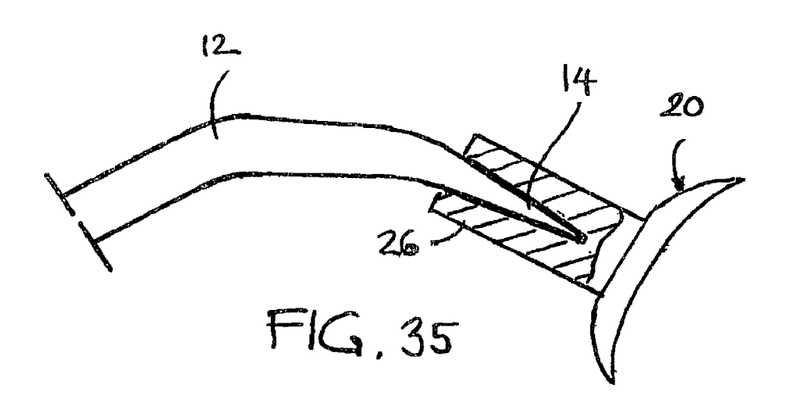
FIG. 35 corresponds to FIG. 32 and presents the coupling element and the tip according to the fifth embodiment.

FIG. 35 illustrates a method of coupling the replaceable tip 20 of the hand instrument 10 wherein the tip 20 is connected directly to a sharp pointed portion 14 at the end of the neck part 12. In this case, the socket 26 in the tip 20 has a shape matching the pointed portion 14.

It is obvious to the person skilled in the art that different embodiments of the invention may be varied within the scope of the claims presented below.

What is claimed is:

1. Dental hand instrument, comprising a handle and a neck part at each end of the handle, each neck part being made of stainless steel and being narrower than the handle and provided with a replaceable tip forming a dental tool, characterized in that
   the end of each neck part of the hand instrument is provided with a coupling element which is an axial socket oriented in the same direction with the neck part and concentric with it,
   the axial socket has at least one groove or slot extending in the longitudinal direction of the socket, and
   each replaceable tip is made of plastic and is provided with an axial projection for cooperating with the axial socket and is oriented in the same direction with the neck part and concentric with it, and wherein each said neck part and replaceable tip provided thereon have substantially the same outer diameter at the end of said neck part where said tip is coupled to said axial socket.

2. Hand instrument as defined in claim 1, characterized in that the axial socket of each neck part has at least two slots extending in the longitudinal direction of the axial socket so that each axial socket has two opposite spring-like tongues for squeezing the projection of the replaceable tip between them.

3. Hand instrument as defined in claim 1, characterized in that an inner surface of each axial socket has a circular or cornered cross-sectional form.

4. Hand instrument as defined in claim 1, characterized in that an inner surface of each axial socket has a quadrangular or hexagonal cross-sectional form.

5. Hand instrument as defined in claim 1, characterized in that each neck part can be bent so as to change the position of the replaceable tip connected to it in relation to the handle of the hand instrument.

6. Hand instrument as defined in claim 1, characterized in that the axial projection of the replaceable tip is provided with at least one locking flange extending in the longitudinal direction of the projection, which flange can be fitted into the at least one groove or slot in the axial socket.

7. Hand instrument as defined in claim 1, characterized in that the axial projection of the replaceable tip is provided with at least two locking flanges extending in the longitudinal direction of the projection, which flanges can be fitted into corresponding grooves or slots in the axial socket.

8. Hand instrument as defined in claim 1, characterized in that the axial projection of the replaceable tip has a circular or cornered cross-sectional form.

9. Hand instrument as defined in claim 1, characterized in that the axial projection of the replaceable tip has a quadrangular or hexagonal cross-sectional form.

10. Hand instrument as defined in claim 1, characterized in that the replaceable tip can be bent so as to allow the tip to be turned into a desired position relative to the handle of the hand instrument.

11. Hand instrument as defined in claim 1, wherein the handle is a hard core coated with a soft material.

12. Hand instrument as defined in claim 11, wherein the soft material is a silicone rubber.

* * * * *